(12) United States Patent
Hoffman et al.

(10) Patent No.: US 12,205,239 B2
(45) Date of Patent: Jan. 21, 2025

(54) INTRALUMINAL IMAGE VISUALIZATION WITH ADAPTIVE SCALING AND ASSOCIATED SYSTEMS, METHODS, AND DEVICES

(71) Applicant: PHILIPS IMAGE GUIDED THERAPY CORPORATION, San Diego, CA (US)

(72) Inventors: Joseph James Hoffman, Sacramento, CA (US); Asher Cohen, San Diego, CA (US); Nili Karmon, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 80 days.

(21) Appl. No.: 17/910,059

(22) PCT Filed: Mar. 1, 2021

(86) PCT No.: PCT/EP2021/055020
§ 371 (c)(1),
(2) Date: Sep. 8, 2022

(87) PCT Pub. No.: WO2021/180501
PCT Pub. Date: Sep. 16, 2021

(65) Prior Publication Data
US 2023/0112722 A1    Apr. 13, 2023

Related U.S. Application Data

(60) Provisional application No. 62/987,545, filed on Mar. 10, 2020.

(51) Int. Cl.
G06T 3/4007    (2024.01)
A61B 8/00      (2006.01)
(Continued)

(52) U.S. Cl.
CPC .......... *G06T 3/4007* (2013.01); *A61B 8/0891* (2013.01); *A61B 8/12* (2013.01); *A61B 8/461* (2013.01)

(58) Field of Classification Search
CPC ....... G06T 3/4007; A61B 8/0891; A61B 8/12; A61B 8/461
See application file for complete search history.

(56) References Cited

U.S. PATENT DOCUMENTS 6,200,268 B1    3/2001  Vince
6,381,350 B1    4/2002  Klingensmith
(Continued)

OTHER PUBLICATIONS

International Search Report and Written Opinion of PCT/EP2021/055020, dated May 17, 2021.
(Continued)

*Primary Examiner* — Daniel F Hajnik

(57) ABSTRACT

Systems, methods, and devices are provided for automatically adjusting the scale or magnification of an intraluminal image on a display of an intraluminal imaging system based on a measured or computed size of the vessel. For example, a system may include a processor configured to receive, from an intraluminal imaging catheter or guidewire, a first intraluminal image of a body lumen, and compute a dimension of an anatomical feature of the body lumen based on the first intraluminal image. The processor computes a scaling factor for the first intraluminal image based on the dimension of the body lumen, scales the first intraluminal image by the scaling factor, and outputs the scaled first intraluminal image to a display in communication with the processor circuit.

35 Claims, 9 Drawing Sheets

(51) Int. Cl.
*A61B 8/08* (2006.01)
*A61B 8/12* (2006.01)

(56) References Cited

U.S. PATENT DOCUMENTS

| | | | |
|---|---|---|---|
| 7,074,188 B2 | 7/2006 | Nair | |
| 7,175,597 B2 | 2/2007 | Vince | |
| 7,215,802 B2 | 5/2007 | Klingensmith | |
| 7,359,554 B2 | 4/2008 | Klingensmith | |
| 7,463,759 B2 | 12/2008 | Klingensmith | |
| 7,846,101 B2 | 12/2010 | Eberle | |
| 7,930,014 B2 | 4/2011 | Huennekens | |
| 8,298,147 B2 | 10/2012 | Huennekens | |
| 2005/0228252 A1* | 10/2005 | Neason | A61B 5/411 600/407 |
| 2006/0177133 A1* | 8/2006 | Kee | A61B 6/463 382/173 |
| 2011/0033098 A1* | 2/2011 | Richter | G06T 7/33 600/443 |
| 2014/0100454 A1* | 4/2014 | Kemp | A61B 8/483 600/407 |
| 2015/0073279 A1 | 3/2015 | Cai | |
| 2020/0013164 A1 | 1/2020 | Elmaanaoui | |
| 2020/0029932 A1 | 1/2020 | Cohen | |
| 2020/0129144 A1* | 4/2020 | Rajguru | A61B 8/0891 |

OTHER PUBLICATIONS

Glaßer, Sylvia et al "Combined Visualization of Wall Thickness and Wall Shear Stress for the Evaluation of Aneurysms", IEEE Transactions on Visualization and Computer Graphics, vol. 20, No. 12, Dec. 2014.

Hammouche, Abdelaziz et al "Automatic IVUS lumen segmentation using a 3D adaptive helix model", Computers in Biology and Medicine, vol. 107, 2019, pp. 58-72.

Ughi, Giovanni et al "Fully Automatic Three-Dimensional Visualization of Intravasculr Optical Coherence Tomography Images: Methods and Feasibility in Vivo", Biomedical Otics Express, 2012 Optical Society of America.

* cited by examiner

INTRALUMINAL IMAGE VISUALIZATION WITH ADAPTIVE SCALING AND ASSOCIATED SYSTEMS, METHODS, AND DEVICES

TECHNICAL FIELD

The subject matter described herein relates to a system for medical imaging. In particular, the present disclosure describes aspects related to acquisition and display of intraluminal medical images obtained by an intraluminal imaging catheter or guidewire. The disclosed systems, methods, and devices have particular but not exclusive utility for diagnosis and treatment of vascular diseases.

BACKGROUND

Various types of intraluminal imaging systems are used in diagnosing and treating diseases. For example, intravascular ultrasound (IVUS) imaging is used as a diagnostic tool for visualizing vessels within a body of a patient. IVUS imaging is carried out with an IVUS catheter or guidewire including one or more ultrasound transducers. The IVUS catheter may be passed into the vessel and guided to the area to be imaged. The transducers emit ultrasonic energy and receive ultrasound echoes reflected from the vessel. The ultrasound echoes are processed to create an image of the vessel of interest. The IVUS images may aid in assessing diseased vessels such as arteries or veins within the human body, determining the need for treatment, optimizing treatment, and/or assessing the effectiveness of a treatment.

Different diseases or medical procedures produce physical features with different size, structure, density, water content, and accessibility for imaging sensors. For example, a deep-vein thrombosis (DVT) produces a clot of blood cells, whereas post-thrombotic syndrome (PTS) produces webbing or other residual structural effects in a vessel that have similar composition to the vessel wall itself, and may thus be difficult to distinguish from the vessel wall. Arteries, such as coronary or peripheral arteries, can exhibit plaque buildup or lesions which constrict the cross-sectional area of the arterial lumen and limit the flow of blood through the artery and increase risk of total occlusion. A stent is a dense (e.g., metallic) object that may be placed in a vessel or lumen to hold the vessel or lumen open to a particular diameter. IVUS imaging may be used to visualize these features and structures to, for example, assess the severity of a blockage in a blood vessel and/or ensure proper stent positioning within the vessel.

When an intraluminal imaging system (e.g., an IVUS imaging system) displays an intraluminal image on a display, the scale of the displayed image is typically fixed and based on the depth of view of the ultrasound transducer, regardless of the location and/or size of the imaged lumen. Accordingly, vessels of larger diameter or area occupy a larger area of the display, while lumens of smaller diameter occupy a smaller area of the display, regardless of the anatomical details being imaged. Natural taper of a vessel (whether coronary or peripheral) can thus result in images of lumens captured at different locations that occupy different portions of the display.

The information included in this Background section of the specification, including any references cited herein and any description or discussion thereof, is included for technical reference purposes only and is not to be regarded as subject matter by which the scope of the disclosure is to be bound.

SUMMARY

Disclosed are systems, methods, and devices for automatically adjusting the scale or magnification of an intraluminal image on a display of an intraluminal imaging system based on a measured or computed size of the vessel. The system may be hereinafter referred to as an adaptive vessel visualization system. The adaptive vessel visualization system may include an intraluminal imaging device in communication with a processor. The processor is configured to measure or compute the size of a feature of the lumen, such as an outer wall of a blood vessel. Based on the measured size of the lumen, the processor automatically adjusts the scale or magnification of the image to be output to the display. It will be understood that the systems and methods disclosed herein may have particular, but not exclusive, utility for intravascular ultrasound (IVUS) imaging procedures.

In one embodiment, an intraluminal imaging system comprises: an intraluminal imaging catheter or guidewire configured to be positioned within a body lumen of a patient, and a processor circuit in communication with the intraluminal imaging catheter or guidewire. The processor circuit is configured to: receive, from the intraluminal imaging catheter or guidewire, a first intraluminal image of the body lumen; compute a dimension of an anatomical feature of the body lumen based on the first intraluminal image; compute a scaling factor for the first intraluminal image based on the dimension of the body lumen; scale the first intraluminal image by the scaling factor; and output the scaled first intraluminal image to a display in communication with the processor circuit.

In some embodiments, the anatomical feature comprises a vessel wall. In some embodiments, the dimension is a diameter. In some embodiments, the dimension is a cross-sectional area. In some embodiments, the processor circuit is configured to scale the first intraluminal image automatically. In some embodiments, the processor circuit is configured to scale the first intraluminal image based on an input from a user interface in communication with the processor circuit. In some embodiments, the processor circuit is configured to scale the first intraluminal image by changing a field of view of the intraluminal imaging catheter or guidewire. In some embodiments, the processor circuit is configured to scale the first intraluminal image by changing a magnification of the first intraluminal image on the display. In some embodiments, the processor circuit is configured to scale the first intraluminal image by the scaling factor in real-time.

In some embodiments, the first intraluminal image is obtained at a first position with the body lumen. In some embodiments, the processor circuit is further configured to: receive a second intraluminal image obtained at a different second position within the body lumen, wherein the dimension of the anatomical feature is different at the second position compared to the dimension at the first position; and scale the second intraluminal image such that the anatomical feature is represented as approximately a same size in the scaled second intraluminal image and the second intraluminal image.

According to another embodiment of the present disclosure, a method for scaling intraluminal images includes: receiving, at processor circuit in communication with an intraluminal imaging catheter or guidewire, a first intraluminal image of a body lumen of a patient obtained by the intraluminal imaging catheter while the intraluminal imaging catheter is positioned within a body lumen of a patient; computing, by the processor circuit, a dimension of an anatomical feature of the body lumen based on the first intraluminal image; computing a scaling factor based on the dimension of the body lumen; scaling the first intraluminal image by the scaling factor; and outputting, to a display in communication with the processor circuit, the scaled first intraluminal image.

In some embodiments, the anatomical feature comprises a vessel wall or a vessel lumen. In some embodiments, the dimension is a diameter or a cross-sectional area. In some embodiments, the scaling of the first intraluminal image is automatic. In some embodiments, the scaling of the first intraluminal image occurs based on an input from a user interface. In some embodiments, the scaling of the first intraluminal image is achieved by changing a field of view of the intraluminal imaging catheter. In some embodiments, the scaling of the first intraluminal image is achieved by changing a magnification of the first intraluminal image on the display. In some embodiments, the scaling of the first intraluminal image is performed in real-time. In some embodiments, the scaling of the first intraluminal image is performed such that the anatomical feature is represented at a size similar to that of a second intraluminal image in which the dimension of the anatomical feature is different than the dimension of the anatomical feature in the first intraluminal image.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the adaptive vessel visualization system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
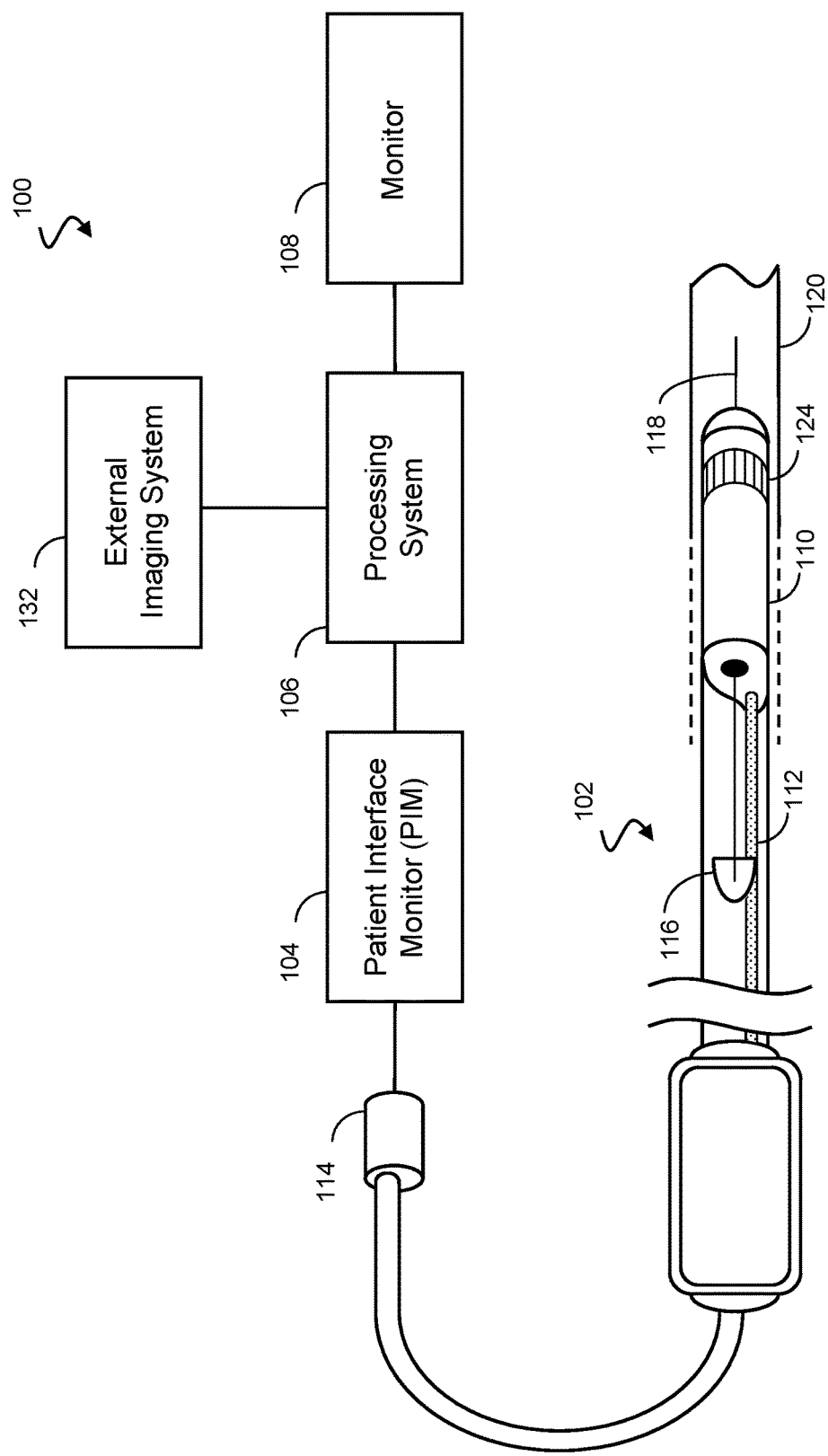
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes systems, devices, and methods for determining a diameter or area of the region of a vessel currently being imaged by an intraluminal imaging probe, and scaling the current intravascular image on a display based on the determined diameter or area, such that vessels of different size occupy approximately the same portion of the display. This feature assists a clinician or other user in viewing and interpreting anatomical details of a vessel having a variety of sizes or diameters, regardless of whether it is large (e.g., a carotid artery or aorta), medium sized, (e.g., an external iliac vein or femoral artery), or small (e.g., a peripheral vein or artery). This may be particularly useful during pullback procedures or other procedures where the intraluminal imaging probe traverses vessels of gradually increasing or decreasing diameter or area. This system, hereinafter referred to as an adaptive vessel visualization system, improves workflows associated with the evaluation and diagnosis of blood vessels within the body. However, although some of the embodiments provided herein may refer specifically to blood vessels, it will be understood that the systems, methods, and devices described herein may be used to visualize, evaluate, and/or diagnose other body lumens, including the esophagus, intestines, or any other suitable body lumen.

In some cases with conventional equipment, a pullback sequence is recorded at maximum field of view (FOV) and displayed in real-time at either maximum FOV or a display FOV selected by the user at the start of a procedure. It may be possible to alter the display FOV of an image during review mode (e.g., after the pullback), but even when this is done, the decision as to what display FOV to use and the selecting of that display FOV are done manually by the clinician or other user. It is an object of the present disclosure to provide systems, methods, and devices that can be used to select and/or dynamically change the display FOV automatically, in real time during the pullback, effectively zooming in or zooming out the image based on the size of the imaged vessel at the longitudinal location of the intraluminal imaging probe.

Embodiments of the present disclosure substantially aid a clinician in viewing, interpreting, measuring, evaluating, and/or diagnosing the health status of blood vessels or other body lumens (e.g., esophagus, intestine, veins, arteries, etc.) within a human body, by magnifying the features of small vessels and/or reducing the features of large vessels such that different vessels or different locations of a vessel occupy approximately the same portion of the display to improve viewability on the display. Implemented on a medical imaging console (e.g., an intraluminal imaging console) in communication with a medical imaging sensor (e.g., an intraluminal ultrasound sensor), the adaptive vessel visualization system disclosed herein may provide both time savings and an improvement in the confidence of diagnoses. This improved imaging workflow transforms raw imaging data into images that are automatically scaled for legibility and interpretability on the display. This may occur without input from the clinician or other user to change the field of view mid-procedure.

The adaptive vessel visualization system may be implemented as a set of logical branches and mathematical operations, whose outputs are viewable on a display, and operated by a control process executing on a processor that accepts user inputs from a keyboard, mouse, or touchscreen interface, and that is in communication with one or more medical imaging sensors (e.g., intraluminal ultrasound sensors). In that regard, the control process performs certain specific operations in response to different inputs or selections made by a user at the start of an imaging procedure, and may also respond to inputs made by the user during the procedure. Certain structures, functions, and operations of the processor, display, sensors, and user input systems are known in the art, while others are recited herein to enable novel features or aspects of the present disclosure with particularity.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased vessels, such as arteries or veins, within the human body to determine the need for treatment, to optimize treatment, and/or to assess a treatment's effectiveness (e.g., through imaging of the vessel before and after treatment).

In some cases, intraluminal imaging is carried out with an IVUS device including one or more ultrasound transducers. The IVUS device may be positioned within the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel. A stent may be placed within the vessel to treat these blockages and intraluminal imaging may be carried out to view the placement of the stent within the vessel. Other types of treatment include thrombectomy, ablation, angioplasty, pharmaceuticals, etc.

Difficulties can arise when performing an imaging pullback over a vessel that changes in size from the distal to the proximal end. The problem may be that at the distal end of the pullback, the vessel is very small and would be appropriate for a small field-of-view, but at the proximal end of the pullback the vessel is very large and would be appropriate for a large field-of-view, or vice-versa. Interpreting the anatomical details of a vessel can become increasingly challenging as the vessel narrows, and the image of the vessel becomes smaller and less detailed on the display. One solution for this problem is either for the user to choose a single field-of-view and accept that one or both ends will not be well visualized, or alternatively to modify the field-of-view during review (if permitted by the system). Neither of these solutions allow optimal visualization during the pullback, and both require manual intervention by the user.

The adaptive vessel visualization system disclosed herein accommodates the decrease in image size by adaptively changing the field-of-view during the pullback so that the vessel is depicted at a scale that is appropriate or optimized for the display and/or graphical interface. In some embodiments, no user intervention is required to achieve this benefit of scaling the image to a relatively constant size, regardless of the diameter or area of the vessel or body lumen being imaged. In some embodiments, an adaptive vessel visualization feature is turned on and off by inputs from the user via the user interface. The adaptive vessel visualization system may lessen the dependency of vascular surgeons on review of magnified images by combining imaging and display functionalities in a novel way to meet an unmet user need. The combined functionalities include automated vessel size detection and field-of-view change or image magnification that is based on the vessel size.

For example, on an IVUS imaging system, a feature may added to enable adaptive field-of-view during IVUS record mode (pullback). When the user enables this feature (by, e.g., selecting an input on a user interface device), an image processing algorithm is applied to determine the size of the vessel to be displayed. In some aspects, the image processing algorithm may be applied in real-time. Based on the determined size of the vessel (e.g., diameter of outer wall), the system automatically changes the field-of-view. For example, the system may automatically and dynamically scale the image such that the outer wall of the vessel appears to be the same size, or approximately the same size, even though the actual size of the vessel varies in the images. In some aspects vessel border detection algorithms may be used for the vessel size estimation. In some embodiments, the border detection algorithms are configured to run in real time. In some embodiments, because the algorithm does not necessarily rely on a detailed border shape or contour (only an estimate of the size), a border detection algorithm may be modified, simplified, and/or optimized such that it can run on the IVUS imaging system in real time. This concept can be implemented for example as a software update to pre-existing hardware.

In other embodiments, the vessel size may be determined by image processing of external images (e.g., angiogram) of the vessel, which may or may not be co-registered with an IVUS image using existing co-registration technology. This concept can also be embodied on OCT or other intravascular imaging modalities. Accordingly, in some aspects, embodiments of the present disclosure provide novel and efficient approaches to FOV and image scaling. This may be relevant for both coronary and peripheral cases, but may be particularly relevant and beneficial in the peripheral vasculature.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the adaptive vessel visualization system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient, such as a blood vessel. For example, the intraluminal device 102 may be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the body lumens or vasculature of a patient. In some embodiments, the intraluminal imaging system 100 is an intraluminal ultrasound (IVUS) imaging system. In other embodiments, the intraluminal imaging system 100 may include foe example systems configured for forward looking intravascular ultrasound (FL-IVUS) imaging, intravascular photoacoustic (IVPA) imaging, intracardiac echocardiography (ICE), transesophageal echocardiography (TEE), optical coherence tomography (OCT), and/or other suitable imaging modalities.

It is understood that the system 100 and/or device 102 can be configured to obtain any suitable intraluminal imaging data. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with a vessel 120. The device 102 may be sized and shaped (and/or configured) for insertion into the vessel 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a vessel 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 100,000 acoustic elements, including values such as 2 acoustic elements, 4 acoustic elements, 36 acoustic elements, 64 acoustic elements, 128 acoustic elements, 500 acoustic elements, 812 acoustic elements, 1,000 acoustic elements, 10,000 acoustic elements, 65,000 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel 120, such as a cross-sectional IVUS image of the vessel 120, is displayed on the monitor 108. Vessel 120 may represent fluid filled or fluid-surrounded structures, both natural and man-made. Vessel 120 may be within a body of a patient. Vessel 120 may be an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Philips and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the vessel 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a vessel and potential for a stent, as well as a post-stent inspection to determine the status of a stent that has been positioned in a vessel. The workflow may be presented to a user in a display screen, such as the example the displays or visualizations shown in FIGS. 5-8.

The external imaging system 132 can be configured to obtain x-ray, radiographic, angiographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
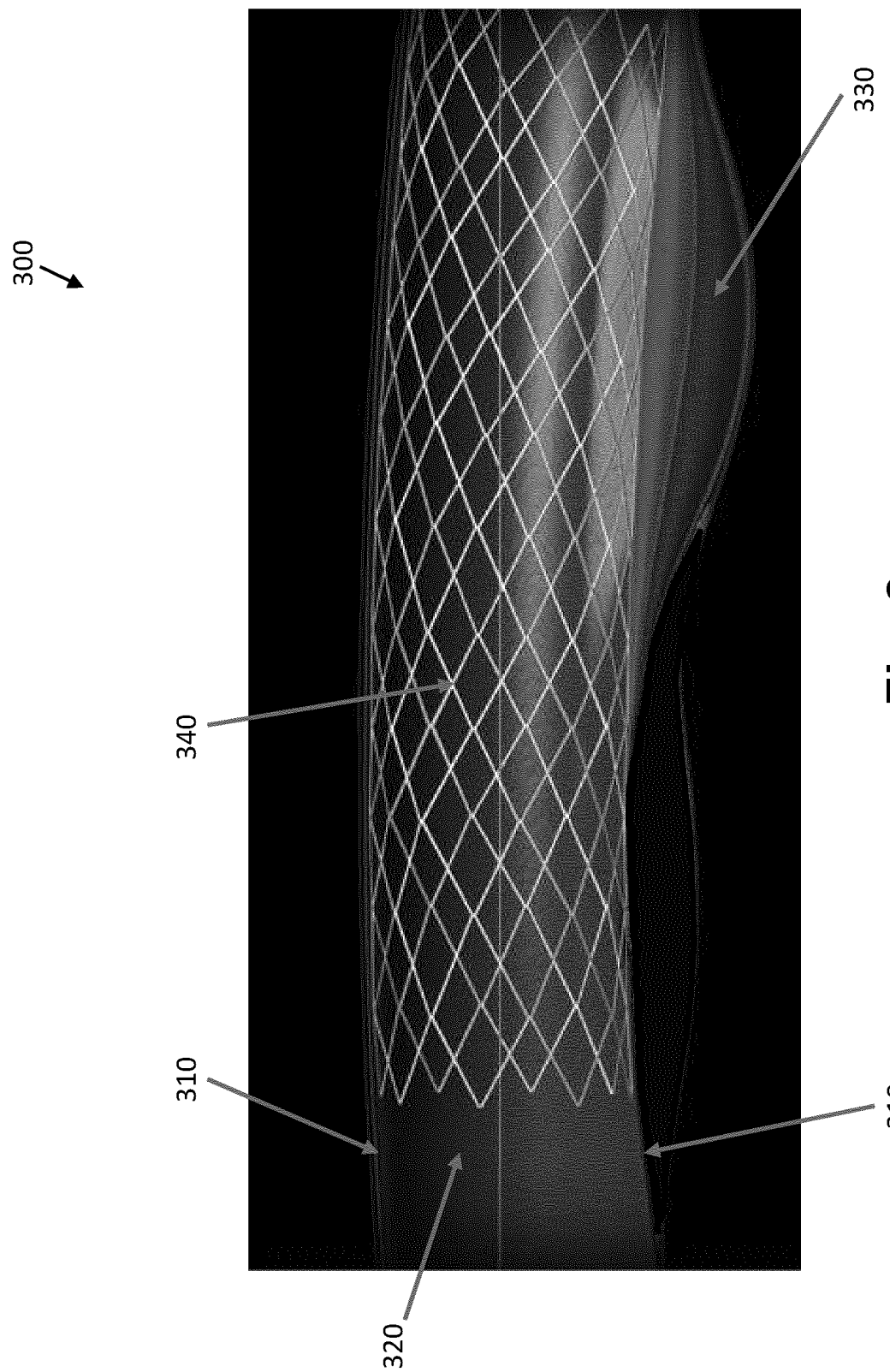
FIG. 2 illustrates a blood vessel incorporating a thrombus and propped open with a stent, according to aspects of the present disclosure.

FIG. 2 illustrates a blood vessel 300 incorporating a thrombus 330 and dilated or propped open with a stent 340. The thrombus occurs between the vessel walls 310 and may restrict the flow of blood 320. Thrombuses come in many types, including sub-acute thrombus, acute thrombus, and chronic thrombus.

The stent 340 compresses and displaces the thrombus 330, opening the blood vessel 300 and preventing the thrombus 330 from traveling through the blood vessel 300. The stent 340 also pushes the vessel walls 310 outward, thus reducing the flow restriction for the blood 320. Other treatment options for alleviating an occlusion may include but are not limited to thrombectomy, ablation, angioplasty, and pharmaceuticals. However, in a large majority of cases it may be highly desirable to obtain accurate and timely intravascular images of the affected area, along with accurate and detailed knowledge of the location of the affected area prior to, during, or after treatment. Inaccurate or imprecise location or orientation information for IVUS images may, for example, carry a risk of ablation or stenting of healthy tissue instead of diseased tissue during treatment.

Build-up of plaque (e.g., arterial stenosis, plaque buildup, thrombus, DVT, chronic total occlusion or CTO, etc.) is one way in which the cross-sectional area of the vein in the peripheral vasculature (e.g., torso, abdomen, groin, leg) may be reduced. Other anatomy that contacts the vein can also reduce its cross-sectional area, thereby restricting blood flow there through. For example, arteries or ligaments in the torso, abdomen, groin, or leg can press against a vein, which changes the shape of the vein and reduces its cross-sectional area. Such reductions in cross-sectional area resulting from contact with other anatomy can be referenced as compression, in that the walls of the vein are compressed as a result of the contact with the artery or ligament.

During for example a pullback procedure where the intraluminal probe 102 begins in a narrower vessel and ends in a wider vessel, the diameter of the vessel increases over the course of the pullback. This would normally result in the vessel appearing progressively larger on the display or monitor 108 during the pullback such that the vessel occupies a larger portion of the display 108. The present disclosure provides systems, methods, and devices that allow for automatic adaptive vessel visualization, which may be initiated by a user input received via a user interface, to adjust the size of the displayed image by adjusting an FOV or magnification setting based on a measured/computed diameter or cross-sectional area of the vessel. Thus, in accordance with embodiments of the present disclosure, the vessel may be displayed with a substantially consistent image size such that the vessel occupies a similar portion or amount of a display (e.g., within a range from ±1% to ±20%, including values such as ±5% and ±10%), regardless of changes in the actually measured or calculated diameter or cross-sectional area of the vessel. This aids a clinician in visualizing vessel details with equal ease, regardless of the size of the vessel.

Figure 3:
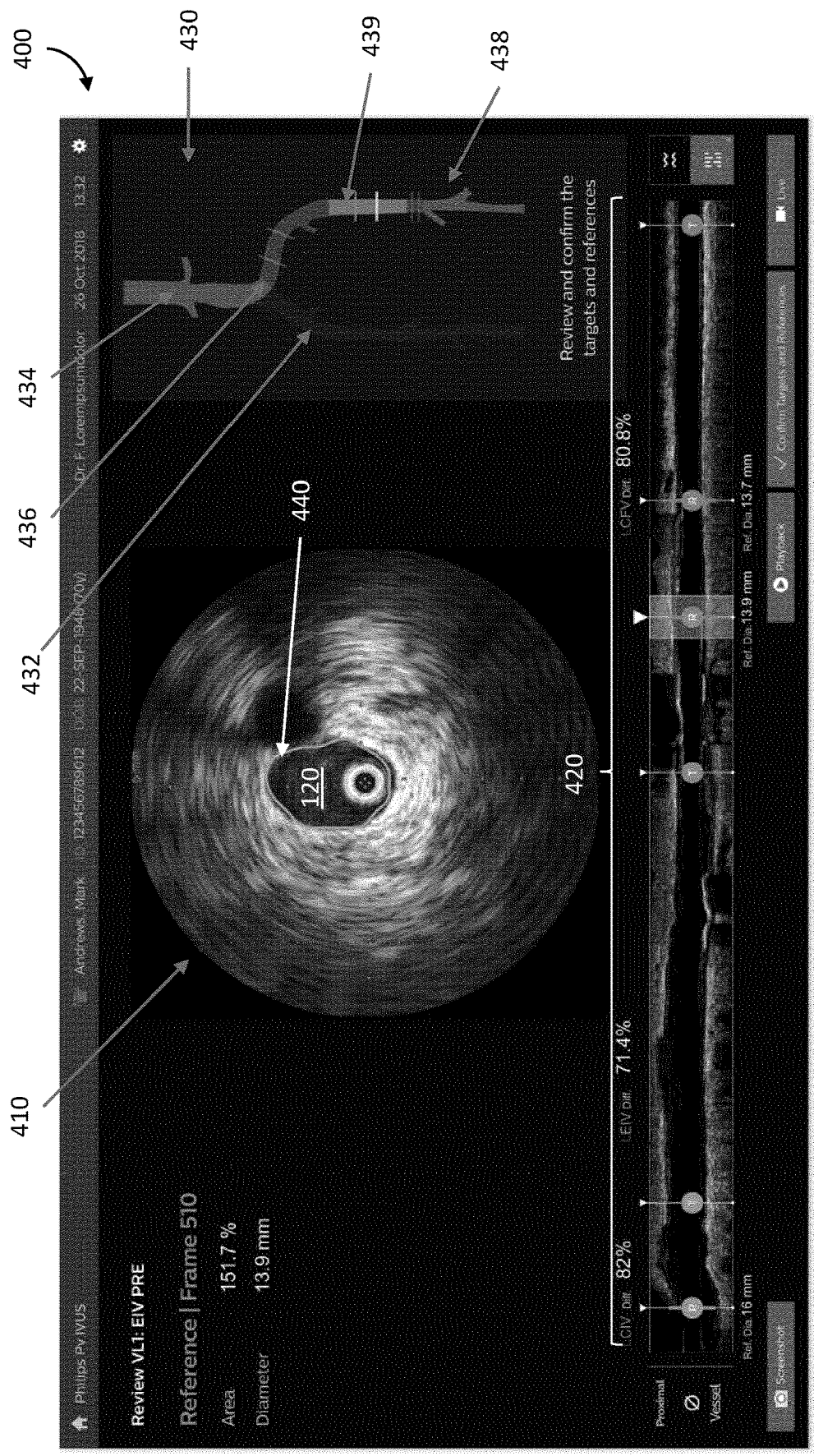
FIG. 3 is a screenshot generated by an intraluminal imaging system incorporating a tomographic image of a lumen in accordance with at least one embodiment of the present disclosure.

FIG. 3 is a screenshot 400 obtained by an intraluminal imaging system incorporating a tomographic image 410 of a vessel 120 in accordance with at least one embodiment of the present disclosure. The screenshot 400 also includes a graphical roadmap 430 and image longitudinal display (ILD) 420. The image longitudinal display 420 is made up from longitudinal cross sections from a plurality of tomographic IVUS images 410 (each representing a lateral or radial cross-sectional view of the vessel 120) captured at different positions along the vessel 120. In this example, the left side 432 of the graphical roadmap 433 (e.g., representing the patient's right leg) is displayed in a very faint color (e.g., dark gray against a black background), to indicate that the right side of the body is not under examination during the current procedure. The inferior vena cava 434, common iliac vein 436, and common femoral vein 438 are displayed in a more visible color (e.g., a lighter gray), to show they are along the path of the current pullback procedure, and the external iliac vein 439 is highlighted in a color (e.g., blue) for emphasis (e.g., because this is the segment is currently being viewed by the intraluminal imaging probe. Other coloring or highlighting schemes may be used instead or in addition. Further, it will be understood that the graphical roadmap 430 may be representative of any body lumen or blood vessel, including coronary and/or peripheral arteries. For example, in some embodiments, the branches of the roadmap 430 may represent the branches of a coronary artery.

Also visible is a detected border 440 of the lumen of the vessel 120. Notably, at the magnification or field of view setting used to capture this tomographic image 610, the vessel border 440 occupies a relatively small portion of the tomographic image 610. A greater magnification setting or smaller FOV setting would increase the size of the vessel in the tomographic image 610, making details of the vessel's anatomy easier for a clinician or other user to see.

Figure 4:
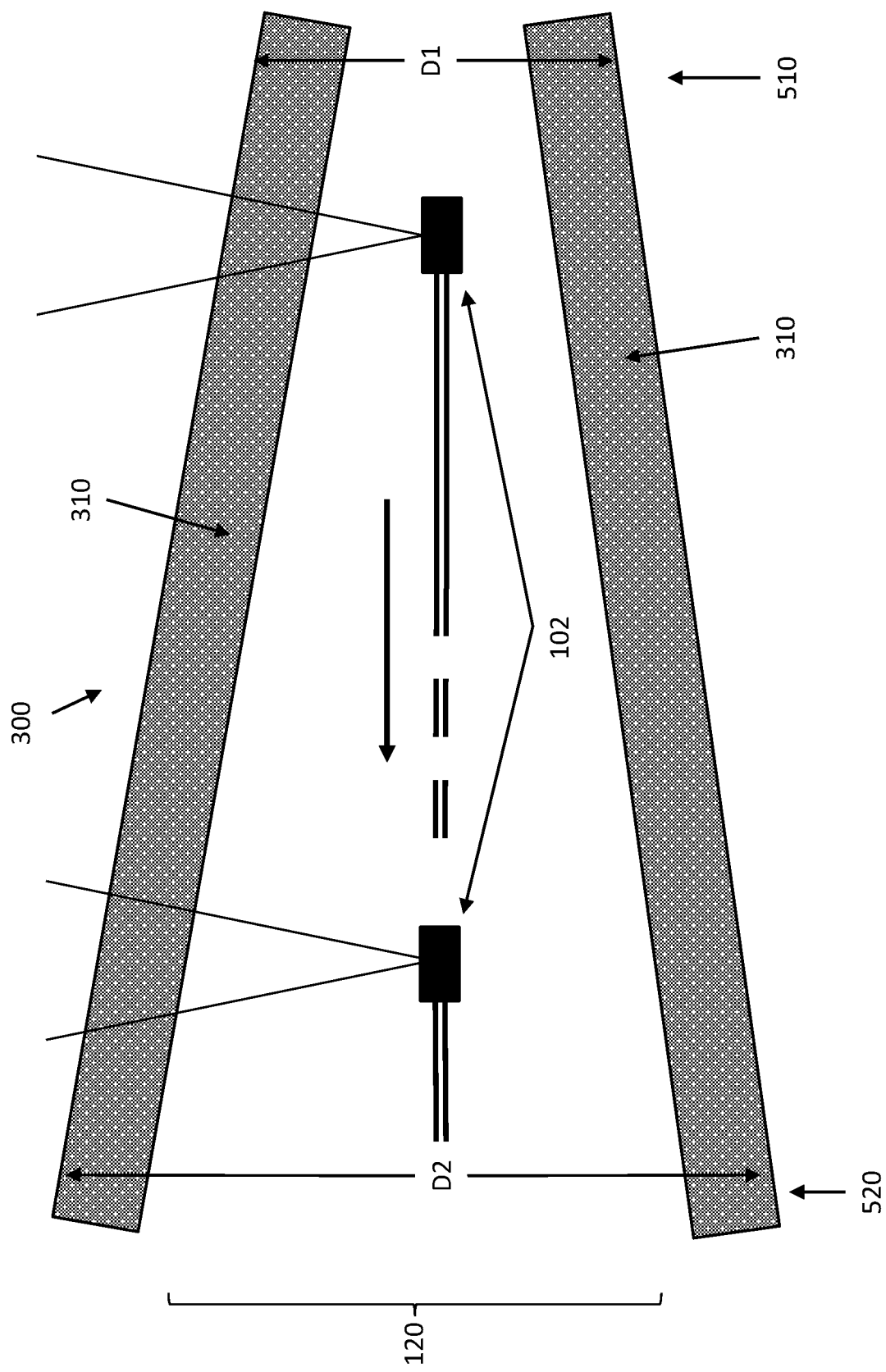
FIG. 4 is a diagrammatic cross-sectional view of an intraluminal imaging probe being pulled back through a vessel that includes a natural taper, in accordance with aspects of the present disclosure.

FIG. 4 is a diagrammatic longitudinal cross-sectional view of an intraluminal imaging probe 102 being pulled back through a vessel 300 that includes a natural taper, in accordance with aspects of the present disclosure. The vessel includes a vessel wall 310 with an outer surface 320. The outer surface 320 of the vessel wall 310 defines the outermost boundary of the vessel 300, and thus the vessel diameter is measured from the outer surface 320 on one side to the outer surface 320 on the other side. This vessel diameter, measured from the outer surface 320 of the vessel wall 310, may be more useful than lumen diameter, as lumen diameter is subject to greater variability in the vicinity of diseased tissue within the vessel 300. However, it will be understood that any diameter or vessel measurement may be used, including the lumen diameter, a diameter measured from the intima, the media, the adventitia, the endothelium, or any other suitable portion of the vessel. The natural taper of the vessel 300 is such that the vessel wall 310 encloses a narrower lumen at a distal portion 510 than it does at a wider, proximal portion 520. The vessel thus has a narrower diameter D1 at the distal portion 510 and a wider diameter D2 at the proximal portion 520. Where the pullback is performed at a constant FOV or magnification setting, and from a more distal to a more proximal location within the vessel 300, this may result in the tomographic ultrasound images of the vessel 300 appearing larger and larger on the monitor as the pullback progresses proximally. However, as described below, the present disclosure describes embodiments that allow for the FOV or magnification to be changed automatically in response to the vessel diameter, such that smaller vessels or vessel regions are viewed with a smaller FOV or greater magnification, while larger vessels or vessel regions are viewed with a larger FOV or smaller magnification. Accordingly, the tomographic ultrasound images may exhibit a relatively constant size on the monitor as the pullback progresses.

Figure 5B:
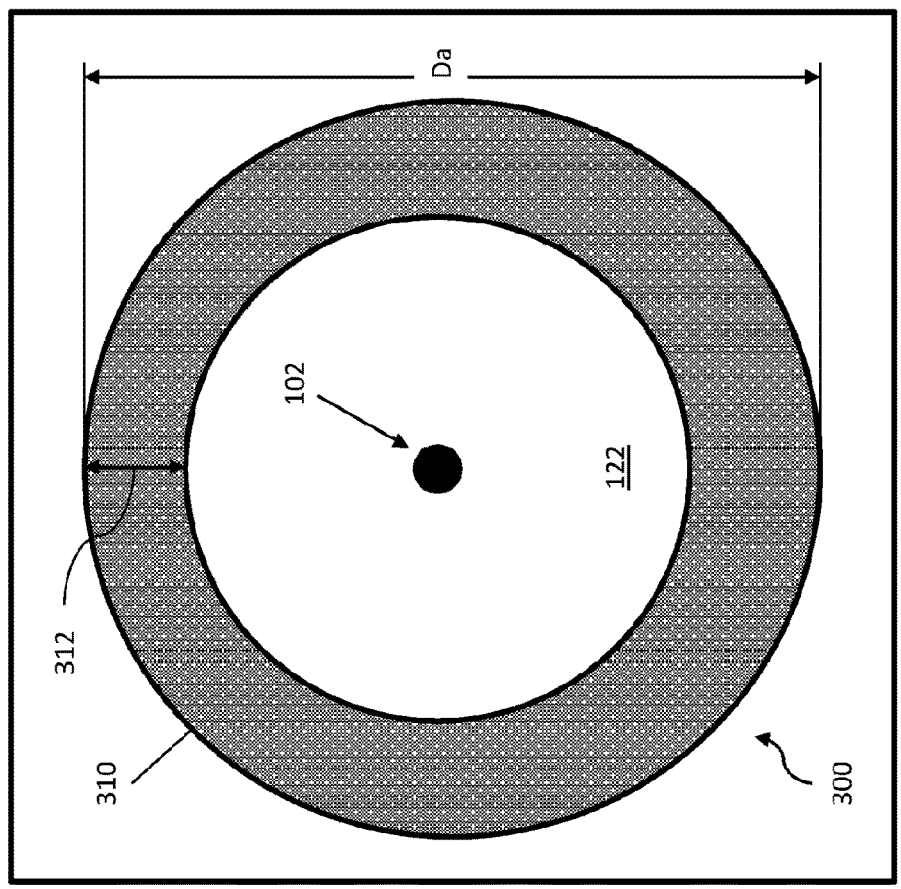
FIG. 5b is a diagrammatic, cross-sectional view of a more proximal portion of the vessel, in accordance with aspects of the present disclosure.
Figure 5A:
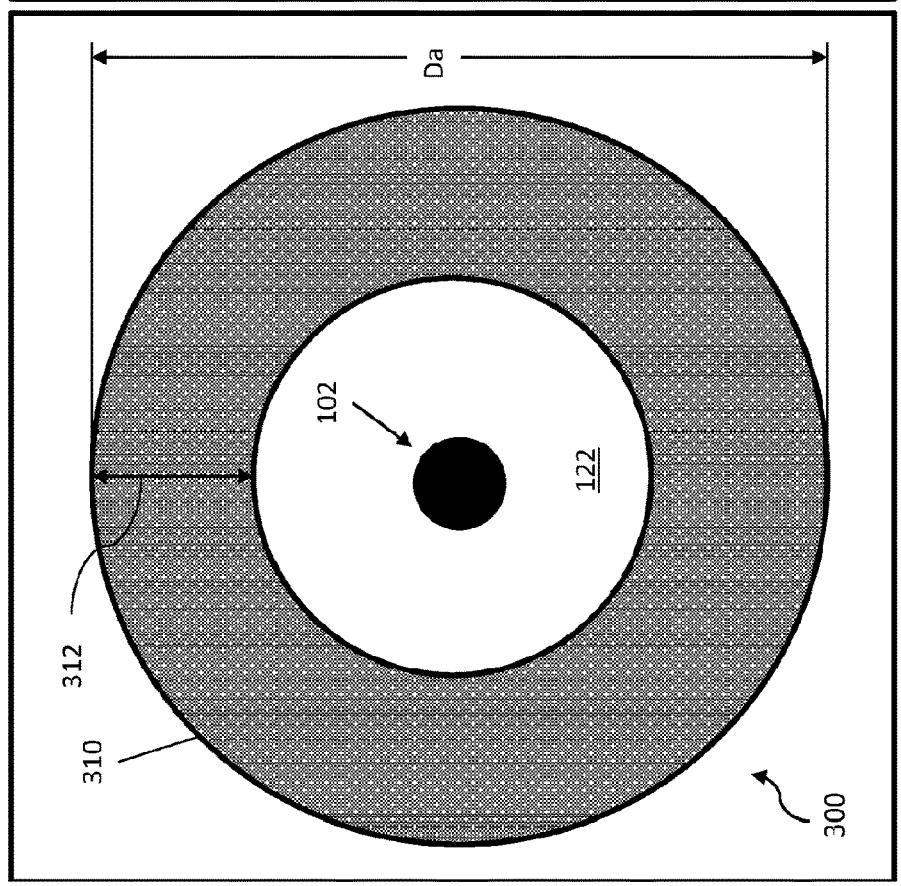
FIG. 5a is a diagrammatic, cross-sectional view of a distal portion of a vessel, in accordance with aspects of the present disclosure.

FIG. 5a is a diagrammatic, cross-sectional view of an automatically scaled image of the distal portion 510 of the vessel 300 as shown in FIG. 4, in accordance with aspects of the present disclosure. Referring to FIG. 5a, the vessel 300 is displayed to have a thickness 312, and an apparent diameter of Da, which may be a function of both the actual diameter D1 of the vessel at the distal portion and the given FOV or magnification setting (which may, for example, relate a certain number of screen pixels to a certain number of millimeters of tissue). Also visible are the vessel wall 310, vessel lumen 122, and the intraluminal imaging probe 102. The view shown in FIG. 5a may, for example, be representative of a tomographic image captured early in a pullback procedure that progresses from the distal portion 510 to the proximal portion 520 within the vessel 300, as shown in FIG. 4.

FIG. 5b is a diagrammatic, cross-sectional view of the proximal portion 520 of the vessel 300 as shown in FIG. 4, in accordance with aspects of the present disclosure. In this example, although the proximal portion 520 of the vessel 300 is wider than the distal portion 510 of the vessel (e.g., its diameter D2 is larger than the vessel diameter D1 of the distal portion 510), the view of FIG. 5b displays the vessel 300 with a higher magnification or smaller FOV, calculated based on the measured diameter D2 of the vessel at this point along the pullback, such that the vessel exhibits at least approximately the same apparent diameter Da as the image in FIG. 5a (e.g., within a range from ±1% to ±20%, including values such as ±5%, ±10%, or any other suitable range). Accordingly, the view of FIG. 5b occupies the same amount or approximately the same amount of the display or graphical user interface. Further, as a result of the reduction in magnification (or increase in FOV), the thickness 312 of the vessel wall 310 and intraluminal imaging probe 102 both appear proportionally smaller in the view of FIG. 5b than they do in FIG. 5a.

Figure 6:
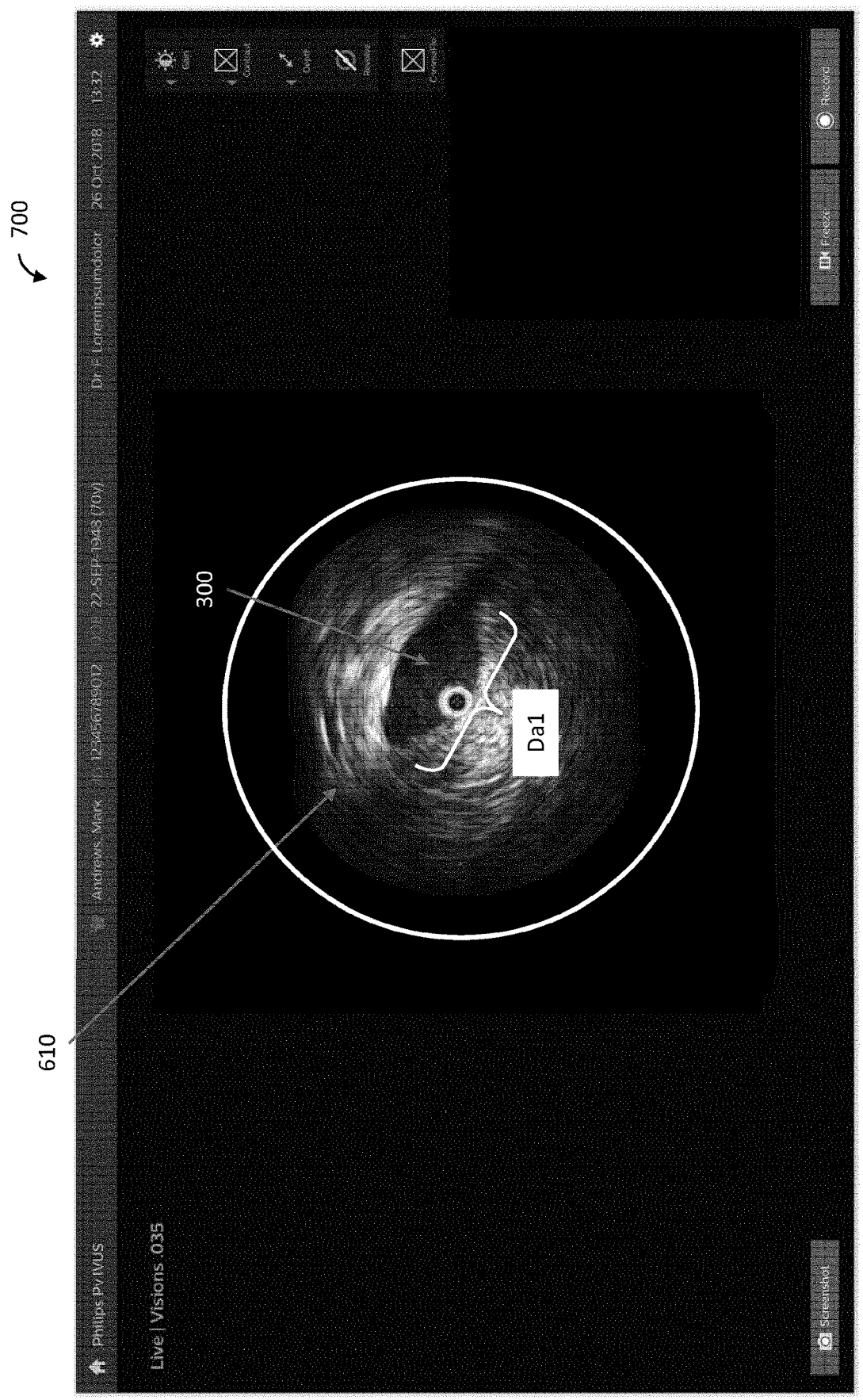
FIG. 6 is a screenshot of a screen display of an example intraluminal imaging system in accordance with at least one embodiment of the present disclosure.

FIG. 6 is a screenshot of a screen display 700 or graphical interface of an example intraluminal imaging system 100 in accordance with at least one embodiment of the present disclosure. Visible is a tomographic image 610 (e.g., a B-mode ultrasound image) of a vessel 300 captured by the intraluminal imaging probe 102 for a given FOV setting, which is typically determined at the start of the imaging procedure. In this example, the image 610 is not automatically scaled and thus the vessel 300 does not occupy the available display area on the screen display 700, but rather exhibits a smaller apparent diameter Da1 that is proportional to the diameter of the vessel 300.

Figure 7:
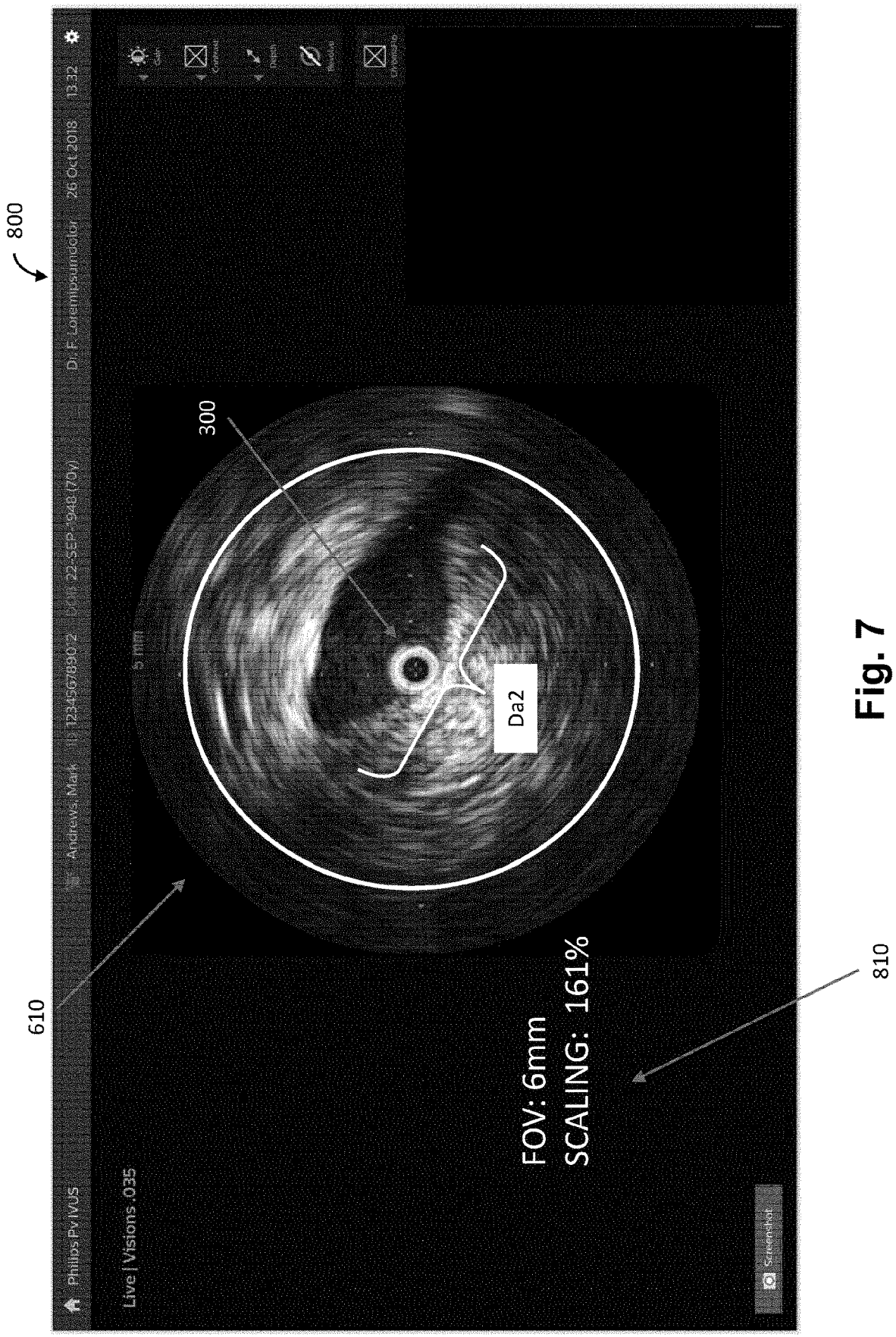
FIG. 7 is a screenshot of a screen display of an example intraluminal imaging system, in accordance with at least one embodiment of the present disclosure.

FIG. 7 is a screenshot of a screen display 800 of an example intraluminal imaging system 100 in which the tomographic image 610 is automatically scaled to occupy an available portion of the display 800, in accordance with at least one embodiment of the present disclosure. Visible is the tomographic image 610 from FIG. 7, of a vessel 300 captured by the intraluminal imaging probe 102. In this example, an FOV, depth of field, or magnification setting has been altered in real-time during the pullback (as opposed to later, during playback), such that the tomographic image 610 has been automatically scaled or magnified so the vessel has an apparent diameter of Da2, which is larger than Da1. Accordingly, in FIG. 7, the automatically scaled image 610 occupies a larger portion of the available display area of the screen display 800, and details of the vessel 300 may be more easily interpreted by a clinician or other user. In an example, the degree of magnification or scaling is based on a scaling factor that is proportional to a ratio of the measured or computed diameter of the vessel 300 to a reference diameter. Vessel diameter rather than lumen diameter is used, because diseased vessels may have thick walls (e.g., due to plaque) and small lumens, and it is necessary to capture the details of the walls regardless of varying lumen size in diseased areas. For example, if the reference diameter is 16 millimeters, then a vessel 300 with a diameter of 16 millimeters is displayed at a standard magnification to fill a certain area of the screen display 800, whereas a vessel with a diameter of 32 millimeters is displayed at −50% or 0.5× of the standard scaling (i.e., half-size), and a vessel with a diameter of 8 millimeters is displayed at +100% or 2> the standard magnification (i.e., double size), such that the apparent diameter Da2 of the vessel in the tomographic image 610 remains relatively constant on the display screen 800 visible on the monitor 108, regardless of the actual dimensions of the vessel 300 or the lumen of the vessel 300 being imaged by the intraluminal imaging probe 102. In some embodiments, cross-sectional area may be used for scaling in place of diameter, or in addition to diameter.

In an example, the diameter or area of a vessel is determined using image recognition to identify and locate the outer border of the vessel wall. The diameter may be determined in pixels. In some embodiments, the diameter or area of the vessel may be converted to units of distance based on, for example, a conversion between pixels and millimeters or square millimeters being a linear function of the FOV setting (e.g., in millimeters) of the intraluminal imaging system 100. Because vessel diameter or area is being calculated purely for scaling purposes, and not for clinical decision making such as stent sizing, the calculation can be approximate (e.g., with an allowable error of ±20% or even ±33%), and thus can benefit from fast, simple recognition and calculation algorithms that run in real time, as well as slower, more accurate recognition and calculation algorithms that may run in near real time, or that may run in the background to determine automatic scaling values for each image in review mode, after the pullback is complete.

Examples of different border detection, image processing, image analysis, and/or pattern recognition algorithms include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety. Other algorithms, whether related to these or not, may be employed instead or in addition. For example, to compute an approximate vessel diameter, it is not necessary to identify the entire border. Rather, it may be sufficient for example to determine a fixed number of different cross sections at fixed orientations, and average the results.

Depending on the implementation, the adaptive vessel visualization system may employ other values for the scaling algorithm, and may employ other magnification algorithms instead or in addition to the one described above. For example, scaling may be based on a vessel cross-sectional area and a reference cross-sectional area, or may be nonlinear. Scaling may be adjusted by holding the magnification constant and changing the FOV of the captured image, or may be adjusted by holding the FOV constant and adjusting the magnification level of the captured image. Optionally, the FOV and/or degree of scaling may be shown in an information box 810 as part of the screen display 800. In an example, scaling the image does not require any changes to the transmit patterns of the ultrasound transducer array 124—only changes to the analysis and display of the received echoes.

Figure 8:
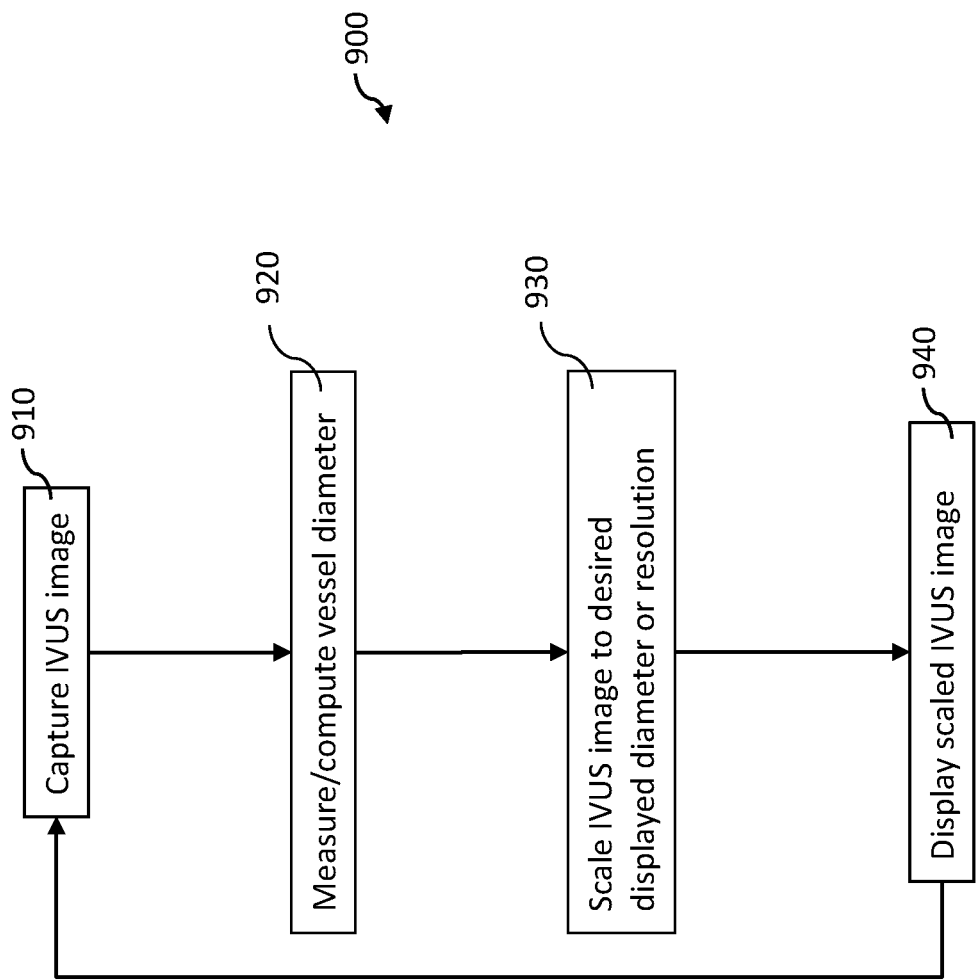
FIG. 8 illustrates a flow diagram for an example adaptive vessel visualization system, in accordance with aspects of the present disclosure.

FIG. 8 illustrates a flow diagram for an example adaptive vessel visualization system 900, in accordance with aspects of the present disclosure. These steps may be executed by an intraluminal imaging system, such as the intraluminal imaging system 100 shown in FIG. 1. For example, the steps may be executed as coded instructions on a processor such as processing system 106 of FIG. 1, and displayed for example on monitor 108 of FIG. 1, in response to inputs by a clinician or other user.

In step 910, an intraluminal imaging system captures a radial cross-sectional intraluminal image, which may also be referred to as a tomographic intraluminal image. Such images may be captured either discretely or continuously during a procedure (e.g., a pullback procedure), and stored within a memory of the processing system.

In step 920, the adaptive vessel visualization system 900 measures or computes a vessel diameter or area. This may be performed for example using depth or range information from the intraluminal imaging probe along with image recognition to identify at least a portion of a blood vessel wall and to distinguish the vessel wall from the surrounding tissue and from the blood flowing within the vessel.

In step 930, the adaptive vessel visualization system scales the tomographic intraluminal image (e.g., by changing the display FOV setting of the intraluminal imaging system) or magnified (e.g., by changing the image magnification on the display) based on the sensed or computed diameter or cross-sectional area of the vessel determined in step 920. In some embodiments, the scaling may be performed such that successive images of the vessel at different longitudinal positions are scaled, magnified, or transformed to be the same size, or approximately the same size, even where the size of the vessel is different at the different longitudinal positions.

In step 940, the system displays the scaled image on the monitor of the intraluminal imaging system. Execution then returns to step 910.

For some embodiments, one or more of the above steps could be eliminated or performed in a different sequence, and other steps may be added. For example, in some embodiments, the system operates in a fully autonomous mode, requiring no input from the user. In other embodiments, the adaptive scaling based on vessel size happens only while a particular control is activated (e.g., when in input is entered on a user input device). In still other embodiments, the adaptive scaling feature is a toggle that can be turned on and off by the user via the user interface. In some embodiments, the steps of the method 900 are performed in real time. In other embodiments, the steps of the method 900 are performed at a later time, after a sequence of intraluminal images has been obtained. For example, the steps of the method 900 may be performed during a post-pullback review of the images obtained during a pullback sequence. In some embodiments, the system is configured to generate a cross-sectional longitudinal image, such as an ILD, based on a plurality of radial cross-sectional intraluminal images (e.g., tomographic images) that have been scaled according to the methods and approaches described above.

Applications for the adaptive vessel visualization system include IVUS education, the use of IVUS systems for treating Peripheral Vascular (PV) disease, and links to other IVUS navigation and visualization systems such as Philips' Vessel Navigator.

Figure 9:
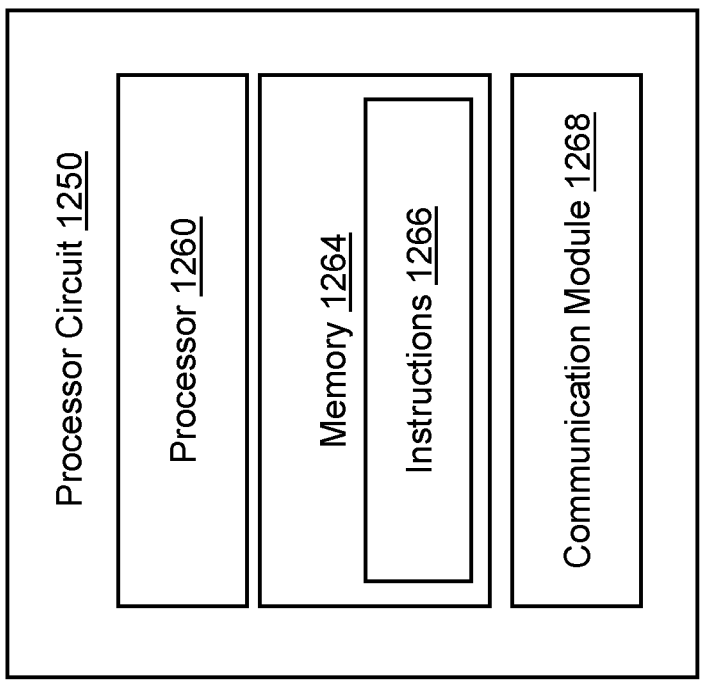
FIG. 9 is a schematic diagram of a processor circuit, in accordance with aspects of the present disclosure.

FIG. 9 is a schematic diagram of a processor circuit 1250, according to aspects of the present disclosure. The processor circuit 1250 may be implemented in the ultrasound imaging system 100, or other devices or workstations (e.g., third-party workstations, network routers, etc.) as necessary to implement one or more methods as disclosed herein, including method 900. As shown, the processor circuit 1250 may include a processor 1260, a memory 1264, and a communication module 1268. These elements may be in direct or indirect communication with each other, for example via one or more buses.

The processor 1260 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1260 may also comprise another hardware device, a firmware device, or any combination thereof configured to perform the operations described herein. The processor 1260 may also be implemented as a combination of computing devices, e.g., a combination of a DSP and a microprocessor, a plurality of microprocessors, one or more microprocessors in conjunction with a DSP core, or any other such configuration.

The memory 1264 may include a cache memory (e.g., a cache memory of the processor 1260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1264 includes a non-transitory computer-readable medium. The memory 1264 may store instructions 1266. The instructions 1266 may include instructions that, when executed by the processor 1260, cause the processor 1260 to perform the operations described herein, including one or more steps of the method 900. Instructions 1266 may also be referred to as code. The terms "instructions" and "code" should be interpreted broadly to include any type of computer-readable statement (s). For example, the terms "instructions" and "code" may refer to one or more programs, routines, sub-routines, functions, procedures, etc. "Instructions" and "code" may include a single computer-readable statement or many computer-readable statements.

The communication module 1268 can include any electronic circuitry and/or logic circuitry to facilitate direct or indirect communication of data between the processor circuit 1250, and other processors or devices. In that regard, the communication module 1268 can be an input/output (I/O) device. In some instances, the communication module 1268 facilitates direct or indirect communication between various elements of the processor circuit 1250 and/or the ultrasound imaging system 100. The communication module 1268 may communicate within the processor circuit 1250 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

A number of variations are possible on the examples and embodiments described above. For example, the adaptive vessel visualization system may be employed in anatomical systems within the body other than those described, or may be employed to image other disease types, object types, or procedure types than those described. The technology described herein may be applied to intraluminal imaging sensors of diverse types (e.g., OCT), whether currently in existence or hereinafter developed. In some embodiments, vessel diameter or area is determined based on a co-registered angiogram image. Aspects of co-registration are described, for example, in U.S. Pat. Nos. 7,930,014 and 8,298,147, the entireties of which are hereby incorporated by reference in its eternity.

Accordingly, the logical operations making up the embodiments of the technology described herein are referred to variously as operations, steps, objects, elements, components, or modules. Furthermore, it should be understood that these may occur in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the adaptive vessel visualization system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the adaptive vessel visualization system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An intraluminal imaging system, comprising:
   an intraluminal imaging catheter or guidewire configured to be positioned within a body lumen of a patient; and
   a processor circuit in communication with the intraluminal imaging catheter or guidewire, wherein the processor circuit is configured to:
   receive, from the intraluminal imaging catheter or guidewire, a first intraluminal image of the body lumen;
   compute a dimension of an anatomical feature of the body lumen in the first intraluminal image;
   compute a scaling factor for the first intraluminal image based on the computed dimension of the anatomical feature and a reference dimension for the anatomical feature, wherein the computed dimension and the reference dimension are each a diameter;
   scale the first intraluminal image by the scaling factor; and
   output the scaled first intraluminal image to a display in communication with the processor circuit.

2. The system of claim 1, wherein the anatomical feature comprises a vessel wall.

3. The system of claim 1, wherein the processor circuit is configured to scale the first intraluminal image automatically.

4. The system of claim 1, wherein the processor circuit is configured to scale the first intraluminal image based on an input from a user interface in communication with the processor circuit.

5. The system of claim 1, wherein the processor circuit is configured to scale the first intraluminal image by changing a field of view of the intraluminal imaging catheter or guide wire.

6. The system of claim 1, wherein the processor circuit is configured to scale the first intraluminal image by changing a magnification of the first intraluminal image on the display.

7. The system of claim 1, wherein the processor circuit is configured to scale the first intraluminal image by the scaling factor in real-time.

8. An intraluminal imaging system, comprising:
   an intraluminal imaging catheter or guidewire configured to be positioned within a body lumen of a patient; and
   a processor circuit in communication with the intraluminal imaging catheter or guidewire, wherein the processor circuit is configured to:
   receive, from the intraluminal imaging catheter or guidewire, a first intraluminal image of the body lumen;
   compute a dimension of an anatomical feature of the body lumen in the first intraluminal image;
   compute a scaling factor for the first intraluminal image based on the computed dimension of the anatomical feature and a reference dimension for the anatomical feature, wherein the computed dimension and the reference dimension are each a cross-sectional area;

scale the first intraluminal image by the scaling factor; and output the scaled first intraluminal image to a display in communication with the processor circuit.

9. The system of claim 8, wherein the anatomical feature comprises a vessel wall.

10. The system of claim 8, wherein the processor circuit is configured to scale the first intraluminal image automatically.

11. The system of claim 8, wherein the processor circuit is configured to scale the first intraluminal image based on an input from a user interface in communication with the processor circuit.

12. The system of claim 8, wherein the processor circuit is configured to scale the first intraluminal image by changing a field of view of the intraluminal imaging catheter or guide wire.

13. The system of claim 8, wherein the processor circuit is configured to scale the first intraluminal image by changing a magnification of the first intraluminal image on the display.

14. The system of claim 8, wherein the processor circuit is configured to scale the first intraluminal image by the scaling factor in real-time.

15. An intraluminal imaging system. comprising:
an intraluminal imaging catheter or guidewire configured to be positioned within a body lumen of a patient; and
a processor circuit in communication with the intraluminal imaging catheter or guidewire, wherein the processor circuit is configured to:
  receive, from the intraluminal imaging catheter or guidewire, a first intraluminal image of the body lumen, wherein the first intraluminal image is obtained at a first position within the body lumen,
  compute a dimension of an anatomical feature of the body lumen in the first intraluminal image;
  compute a scaling factor for the first intraluminal image based on the computed dimension of the anatomical feature and a reference dimension for the anatomical feature;
  scale the first intraluminal image by the scaling factor;
  output the scaled first intraluminal image to a display in communication with the processor circuit;
  receive a second intraluminal image obtained at a different second position within the body lumen, wherein a size of the body lumen changes along a length of the body lumen such that the dimension of the anatomical feature is different at the second position compared to the dimension at the first position; and
  scale the second intraluminal image such that the anatomical feature is represented as a same size in the scaled second intraluminal image and the scaled first intraluminal image.

16. The system of claim 15, wherein the anatomical feature comprises a vessel wall.

17. The system of claim 15, wherein the processor circuit is configured to scale the first intraluminal image automatically.

18. The system of claim 15, wherein the processor circuit is configured to scale the first intraluminal image based on an input from a user interface in communication with the processor circuit.

19. The system of claim 15, wherein the processor circuit is configured to scale the first intraluminal image by changing a field of view of the intraluminal imaging catheter or guide wire.

20. The system of claim 15, wherein the processor circuit is configured to scale the first intraluminal image by changing a magnification of the first intraluminal image on the display.

21. The system of claim 15, wherein the processor circuit is configured to scale the first intraluminal image by the scaling factor in real-time.

22. A method for scaling intraluminal images, comprising:
receiving, at processor circuit in communication with an intraluminal imaging catheter or guidewire, a first intraluminal image of a body lumen of a patient obtained by the intraluminal imaging catheter while the intraluminal imaging catheter is positioned within a body lumen of a patient;
computing, by the processor circuit, a dimension of an anatomical feature of the body lumen in the first intraluminal image;
computing a scaling factor based on the computed dimension of the anatomical feature and a reference dimension for the anatomical feature, wherein the computed dimension and the reference dimension are each a diameter or a cross-sectional area;
scaling the first intraluminal image by the scaling factor; and
outputting, to a display in communication with the processor circuit, the scaled first intraluminal image.

23. The method of claim 22, wherein the anatomical feature comprises a vessel wall or a vessel lumen.

24. The method of claim 22, wherein the scaling of the first intraluminal image is automatic.

25. The method of claim 22, wherein the scaling of the first intraluminal image occurs based on an input from a user interface.

26. The method of claim 22, wherein the scaling of the first intraluminal image is achieved by changing a field of view of the intraluminal imaging catheter.

27. The method of claim 22, wherein the scaling of the first intraluminal image is achieved by changing a magnification of the first intraluminal image on the display.

28. The method of claim 22, wherein the scaling of the first intraluminal image is performed in real-time.

29. A method for scaling intraluminal images, comprising:
receiving, at processor circuit in communication with an intraluminal imaging catheter or guidewire, a first intraluminal image of a body lumen of a patient obtained by the intraluminal imaging catheter while the intraluminal imaging catheter is positioned within a body lumen of a patient, wherein the first intraluminal image is obtained at a first position within the body lumen;
computing, by the processor circuit, a dimension of an anatomical feature of the body lumen in the first intraluminal image;
computing a scaling factor based on the computed dimension of the anatomical feature and a reference dimension for the anatomical feature;
scaling the first intraluminal image by the scaling factor; and
outputting, to a display in communication with the processor circuit, the scaled first intraluminal image, wherein the scaling of the first intraluminal image is performed such that the anatomical feature is represented in the first intraluminal image at a same size that the anatomical feature is represented in a second intraluminal image obtained at a different, second position within the body lumen, and wherein a size of the body lumen changes along a length of the body lumen such that the dimension of the anatomical feature at the first position is different than the dimension of the anatomical feature at the second position.

30. The method of claim 29, wherein the anatomical feature comprises a vessel wall or a vessel lumen.

31. The method of claim 29, wherein the scaling of the first intraluminal image is automatic.

32. The method of claim 29, wherein the scaling of the first intraluminal image occurs based on an input from a user interface.

33. The method of claim 29, wherein the scaling of the first intraluminal image is achieved by changing a field of view of the intraluminal imaging catheter.

34. The method of claim 29, wherein the scaling of the first intraluminal image is achieved by changing a magnification of the first intraluminal image on the display.

35. The method of claim 29, wherein the scaling of the first intraluminal image is performed in real-time.

* * * * *